United States Patent
Heinemann et al.

(10) Patent No.: US 6,350,909 B1
(45) Date of Patent: Feb. 26, 2002

(54) METHOXYMINO-PHENYLACETAMIDE DERIVATIVES AND THEIR UTILIZATION AS PESTICIDES

(75) Inventors: Ulrich Heinemann, Leichlingen; Herbert Gayer, Monheim; Peter Gerdes, Aachen; Martin Vaupel; Astrid Mauler-Machnik, both of Leichlingen; Gerd Hänssler, Leverkusen; Klaus Stenzel, Düsseldorf; Martin Kugler, Leichlingen; Thomas Jaetsch, Köln; Peter Wachtler, Krefeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/720,893

(22) PCT Filed: Jun. 26, 1999

(86) PCT No.: PCT/EP99/04443

§ 371 Date: Jan. 2, 2001

§ 102(e) Date: Jan. 2, 2001

(87) PCT Pub. No.: WO00/02849

PCT Pub. Date: Jan. 20, 2000

(30) Foreign Application Priority Data

Jul. 9, 1998 (DE) .......................................... 198 30 695

(51) Int. Cl.$^7$ ..................... C07C 233/05; C07C 231/02; A01N 37/18

(52) U.S. Cl. ........................ 564/157; 514/327; 514/331; 514/345; 514/352; 514/360; 514/367; 514/385; 514/393; 514/412; 514/438; 514/443; 514/445; 514/456; 514/461; 514/473; 514/616; 546/216; 546/229; 546/290; 546/329; 548/124; 548/146; 548/152; 548/302.7; 549/49; 549/51; 549/65; 549/76; 549/462; 549/475; 549/491; 564/142; 564/144

(58) Field of Search .................. 564/157, 142, 564/144; 514/616, 327, 331, 345, 352, 360, 367, 385, 393, 412, 438, 443, 445, 456, 461, 473; 546/216, 229, 209, 329; 548/124, 146, 152, 302.7; 549/65, 76, 49, 51, 475, 491, 462

(56) References Cited

U.S. PATENT DOCUMENTS

| 5,185,342 A | 2/1993 | Hayase et al. |
|---|---|---|
| 5,248,687 A | 9/1993 | Hayase et al. |
| 5,360,810 A | 11/1994 | Hayase et al. |
| 5,371,223 A | 12/1994 | Hayase et al. |
| 5,401,877 A | 3/1995 | Hayase et al. |

FOREIGN PATENT DOCUMENTS

| WO | 97/00856 | 1/1997 |

*Primary Examiner*—Shailendra Kumar
(74) *Attorney, Agent, or Firm*—Joseph C. Gil

(57) ABSTRACT

The invention relates to new imides, to a plurality of processes for their preparation and to their use as fungicides.

16 Claims, No Drawings

METHOXYMINO-PHENYLACETAMIDE DERIVATIVES AND THEIR UTILIZATION AS PESTICIDES

This application is a 371 of PCT/EP99/04443, filed Jun. 26, 1999.

FIELD OF THE INVENTION

The invention relates to new imides, to a plurality of processes for their preparation, and to their use as fungicides.

BACKGROUND OF THE INVENTION

It is known that certain imides which are similar to those mentioned below have fungicidal properties (cf., for example, EP-A 398692, EP-A 528681 and WO 97-00856). However, the action of these compounds is not entirely satisfactory in all fields of application, in particular when low application rates are used.

SUMMARY OF THE INVENTION

Novel imides have general formula (1)

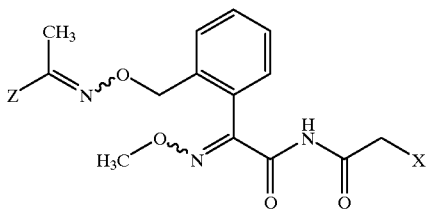

(I)

in which
X represents halogen or alkoxy and
Z represents optionally substituted aryl or a group

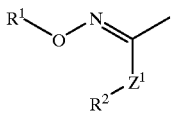

in which
$R^1$ represents optionally substituted alkyl, cycloalkyl or arylalkyl,
$R^2$ represents optionally substituted alkyl, aryl, cycloalkyl, arylalkyl, heterocyclyl or heterocyclylalkyl,
$Z^1$ represents a single bond, oxygen, sulphur or a group

where
$R^4$ represents alkyl, or together with $R^2$ and the nitrogen atom to which they are bonded forms an optionally substituted heterocyclic ring. Aryl represents aromatic, mono- or polycyclic hydrocarbon rings such as by way of example and preferably phenyl, naphthyl, anthranyl, phenanthryl, preferably phenyl or naphthyl, in particular phenyl.

Furthermore, it has been found that the new substituted heterocycloalkenes of the general formula (I) are obtained when
carboxamides of the general formula (II)

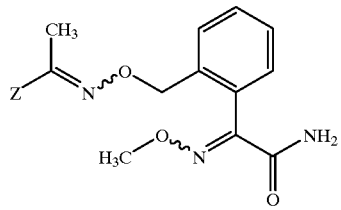

(II)

in which
Z is as defined above,
are reacted with an carbonyl halide of the formula (III),

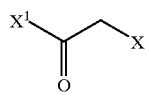

(III)

in which
X is as defined above, and
$X^1$ represents halogen, or
are reacted with a carboxylic anhydride of the formula (IV)

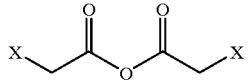

(IV)

in which
X is as defined above,
in each case if appropriate in the presence of a diluent and in each case if appropriate in the presence of an acid binder.

Finally, it has been found that the new carboxamide derivatives of the general formula (I) have a very potent fungicidal action.

If appropriate, the compounds according to the invention may exist as mixtures of various isomeric forms which are possible, in particular stereoisomers such as for example, E- and Z-isomers but, if appropriate, also in the form of tautomers. Claimed are the E- and the Z-isomers, any mixtures of these isomers, and the tautomeric forms which are possible.

The present invention preferably relates to imides of the formula (I) in which
X represents chlorine or alkoxy having 1 to 4 carbon atoms and
Z represents phenyl or naphthyl, each of which is optionally monosubstituted or polysubstituted by identical or different substituents, the substituents which are possible preferably being selected from the list hereinbelow:
halogen, cyano, nitro, hydroxyl, formyl, carboxyl, carbamoyl, thiocarbamoyl;
in each case straight-chain or branched alkyl, alkoxy, alkylthio, alkylsulphinyl or alkylsulphonyl, each of which have 1 to 6 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy each of which has 2 to 6 carbon atoms and 1 to 11 identical or different halogen atoms;

in each case straight-chain or branched alkylcarbonyl, alkylcarbonyloxy, alkoxycarbonyl or alkylsulphonyloxy, each of which has 1 to 6 carbon atoms in the individual alkyl moieties;

in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl, each of which has 3 to 7 ring members of which in each case 1 to 3 are identical or different heteroatoms—in particular nitrogen, oxygen and/or sulphur;

or a group

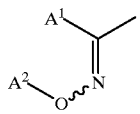

in which $A^1$ represents alkyl with 1 to 4 carbon atoms or cycloalkyl having 1 to 6 carbon atoms and $A^2$ represents alkyl having 1 to 4 carbon atoms, alkenyl or alkinyl, each of which has 2 to 4 carbon atoms, optionally substituted by cyano, alkoxy, alkylthio, alkylamino, dialkylamino or phenyl, Z also represents a group

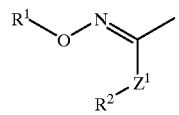

in which $R^1$ represents alkyl having 1 to 12 carbon atoms, cycloalkyl having 3 to 8 carbon atoms which is optionally substituted by halogen or alkyl having 1 to 4 carbon atoms, or arylalkyl having 6 to 10 carbon atoms in the aryl moiety and 1 to 4 carbon atoms in the alkyl moiety, and which is optionally substituted in the aryl moiety, the substituents preferably being selected from the following list:

halogen, cyano, nitro, in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl, each of which has 1 to 8 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

$R^2$ represents alkyl having 1 to 12 carbon atoms, cycloalkyl having 3 to 8 carbon atoms which is optionally substituted by halogen or alkyl having 1 to 4 carbon atoms, or represents heterocyclyl, benzoheterocyclyl, dibenzoheterocyclyl or heterocyclylalkyl, each of which has 3 to 7 ring members in the heterocyclyl moiety and 1 to 4 carbon atoms in the alkyl moiety and each of which is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl;

or represents aryl or arylalkyl having 6 to 10 carbon atoms in the aryl moiety and 1 to 4 carbon atoms in the alkyl moiety, each of which is optionally substituted in the aryl moiety, the substituents preferably being selected from the following list:

halogen, cyano, nitro, amino, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl, each of which has 1 to 8 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy each of which has 2 to 6 carbon atoms and 1 to 11 identical or different halogen atoms;

in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;

cycloalkyl or cycloalkyloxy, each of which has 3 to 6 carbon atoms; in each case divalent alkylene having 3 or 4 carbon atoms, oxyalkylene having 2 or 3 carbon atoms or dioxyalkylene having 1 or 2 carbon atoms, in each case optionally monosubstituted to tetrasubstituted by identical or different substituents from the series consisting of fluorine, chlorine, methyl, trifluoromethyl or ethyl;

phenoxy or phenylalkoxy having 1 to 4 carbon atoms in the alkyl moiety and in each case optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclyloxy, heterocyclylthio, heterocyclylsulphinyl or heterocyclylsulphonyl having 5 or 6 ring members, in each case optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl, or a group

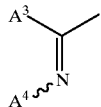

in which
A³ represents hydrogen or alkyl having 1 to 4 carbon atoms or cycloalkyl having 3 to 6 carbon atoms and
A⁴ represents hydroxyl, amino, methylamino, methyl, phenyl, benzyl, alkoxy, alkylamino, dialkylamino having 1 to 4 carbon atoms in the respective alkyl chains,
Z¹ represents a single bond, oxygen, sulphur or a group

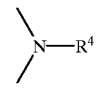

in which
R⁴ represents alkyl having 1 to 4 carbon atoms, or together with R² and the nitrogen atom to which they are bonded forms an optionally substituted, 3 to 6-membered, heterocyclic ring.

In the definitions, the saturated or unsaturated hydrocarbon chains such as alkyl, alkanediyl, alkenyl or alkinyl, also in conjunction with heteroatoms such as in alkoxy or alkylthio are in each case straight-chain or branched.

Halogenoalkyl represents partially or fully halogenated alkyl. In the case of polyhalogenated halogenoalkyl, the halogen atoms can be identical or different. Preferred halogen atoms are fluorine and chlorine, in particular fluorine. If the halogenoalkyl has attached to it yet further substituents, the maximum number of halogen atoms which is possible is reduced to the remaining free valences.

Halogen generally represents fluorine, chlorine, bromine or iodine, preferably fluorine, chlorine or bromine, in particular fluorine or chlorine.

Heterocyclyl represents saturated or unsaturated and also aromatic, cyclic compounds in which at least one ring member is a heteroatom, that is to say atom other than carbon. If the ring contains a plurality of heteroatoms, they may be identical or different. Heteroatoms are preferably oxygen, nitrogen or sulphur. If the ring contains more oxygen atoms, they are not adjacent. If appropriate, the cyclic compounds together with other carbocyclic or heterocyclic, fused or bridged rings form a polycyclic ring system. A polycyclic ring system can be linked via the heterocyclic ring or a fused carbocyclic ring. Preferred are mono- or bicyclic ring systems in particular mono- or bicyclic aromatic ring systems.

In particular, the subject matter of the invention is imides of the formula (I) in which
X represents chlorine, methoxy, ethoxy, n- or i-propoxy, n-, i-, s- or t-butoxy and Z represents phenyl which is optionally substituted, in particular monosubstituted or disubstituted, especially preferably substituted in the 3- and/or 4-position, the substituents which are possible preferably being selected from the following list:
fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, 3-fluoropropen-2-yloxy, methoxycarbonyl, ethoxycarbonyl,
in each case divalent propane-1,3-diyl, butane-1,4-diyl, methylenedioxy or ethylenedioxy, each of which is optionally monosubstituted to tetrasubstituted by identical or different substituents from the series consisting of fluorine, chlorine, methyl, trifluoromethyl or ethyl,
or a group

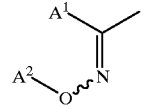

in which
A¹ represents, in particular, methyl, ethyl, n- or i-propyl, n-, i-, s- or t-butyl, cyclopropyl or cyclobutyl, and
A² represents, in particular, methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl,
Z likewise represents a group

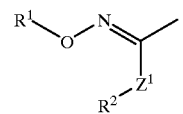

in which
R¹ represents cyclopentyl or cyclohexyl, each of which is optionally monosubstituted to tetrasubstituted by fluorine, chlorine, methyl or ethyl; or
represents cyclopropyl, cyclobutyl, cyclopentyl or cyclohexyl, optionally substituted by methyl, ethyl, fluorine, chlorine or bromine; or represents benzyl, 1-phenylethyl or 2-phenylethyl, each of which is optionally monosubstituted to tetrasubstituted by identical or different substituents, the substituents which are possible preferably being selected from the following list:
fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsuphonyl, $R^2$ represents methyl, ethyl, n- or i-propyl, n-, i-, s- or t-butyl, pentyl, hexyl, heptyl, octyl, nonyl, decyl, undecyl, dodecyl, cyclopentyl or cyclohexyl, each of which is optionally monosubstituted to tetrasubstituted by fluorine, chlorine, methyl or ethyl; or represents thienyl, pyridyl, furyl, piperazinyl, thiazolyl, dioxazinyl, benzimidazolyl, benzothiazolyl, benzofuranyl, benzopyrazolyl, dibenzothiazinyl, thienylmethyl, pyridylmethyl or furylmethyl, optionally substituted by methyl, ethyl, fluorine, chlorine, bromine, trifluoromethyl, phenyl;

or represents phenyl, benzyl, 1-phenylethyl or 2-phenylethyl, each of which is optionally mono- substituted to tetrasubstituted in the phenyl moiety by identical or different substituents, the substituents which are possible preferably being selected from the following list:
fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy; trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy, in each case divalent propanediyl, ethylenoxy, methylenedioxy, ethylenedioxy, each of which is optionally monosubstituted to tetrasubstituted by identical or different substituents from the series consisting of fluorine, chlorine, methyl or trifluoromethyl, phenoxy or benzyl, each of which is optionally substituted by fluorine, chlorine, methyl, trifluoromethyl or methoxy, heterocyclyl, heterocyclyloxy, heterocyclylthio, hetereocyclylsulphinyl or heterocyclylsulphonyl, each of which has 5 or 6 ring members and is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl, or represents thienyl, imidazolyl, thiadiazolyl, pyridyl, furyl, piperazinyl, thiazolyl, dioxazinyl, thiadiazolylsulphonyl, optionally substituted by methyl, ethyl, fluorine, chlorine, bromine, trifluoromethyl, phenyl;

or a group

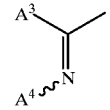

in which
$A^3$ represents hydrogen or methyl and
$A^4$ represents hydroxyl, methoxy, ethoxy, amino, methylamino, methyl, phenyl or benzyl, $Z^1$ represents a single bond, oxygen, sulphur or a group

in which
$R^4$ represents methyl, ethyl, n- or i-propyl, n-, i-, s- or t-butyl, or together with $R^2$ and the nitrogen atom to which they are bonded forms an optionally substituted 5 to 6-membered heterocyclic ring.

$R^1$ preferably represents ethyl, in particular methyl.

$R^2$ preferably represents methyl, ethyl, n- or i-propyl, n-, i-, s- or t-butyl or represents phenyl which is monosubstituted or disubstituted by fluorine, chlorine, methyl, methoxy, trifluoromethyl and/or trifluoromethoxy, in particular unsubstituted phenyl.

Especially preferred compounds are those in which X represents chlorine, in particular methoxy.

Z preferably represents substituted or unsubstituted aryl, in particular phenyl, particularly preferred substituents being alkyl, halogen, halogenoalkyl or halogenoalkoxy.

The substituents are in the 2-, 3- and/or in particular 4-position.

The definitions of the radicals given above in general terms or in the preferred ranges apply to the end products of the formula (I) as also correspondingly to the starting materials or intermediates required in each case for the preparation.

The definitions of radicals given individually for these radicals in the respective combinations, or preferred combinations, of radicals are also, independently of the particular combination given, replaced by any definitions of radicals of others. Moreover, definitions of radicals may also be withdrawn from each preferred range.

Formula (II) provides a general definition of the carboxamides required as starting materials for carrying out the process according to the invention. In this formula (II), X and Z preferably, or in particular, have the meaning which has already been mentioned in connection with the description of the compounds of the formula (I) according to the invention as being preferred, or particularly preferred, for X and Z.

The carboxamides of the formula (II) are known and/or can be prepared by processes known per se (cf., for example, EP-A 398692 and EP-A 528681). Formula (III) provides a general definition of the carbonyl halides furthermore required as starting materials for carrying out the process according to the invention. In this formula (III), X preferably, or in particular, has the meaning which has already been mentioned in connection with the description of the compounds of the formula (I) according to the invention as being preferred, or particularly preferred, for X. $X^1$ represents halogen, preferably chlorine.

The carbonyl halides of the formula (III) are known chemicals for synthesis.

Formula (IV) provides a general definition of the carboxylic anhydrides required as alternative starting materials for carrying out the process according to the invention. In this formula (IV), X preferably, or in particular, has the meaning which has already been mentioned in connection with the description of the compounds of the formula (I) according to the invention as being preferred, or particularly preferred, for X.

The carboxylic anhydrides of the formula (IV) are known chemicals for synthesis.

Diluents which are suitable for carrying out the process according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene, or decalin; halogenated hydrocarbons such as, for example, chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide and sulphones such as sulpholane.

If appropriate, the process according to the invention is carried out in the presence of a suitable acid acceptor. Suitable acid acceptors are all customary inorganic or organic bases. These include, for example, the hydrides, hydroxides, amides, alkoxides, acetates, carbonates or hydrogencarbonates of alkaline earth metals or alkali metals such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogencarbonate, sodium hydrogencarbonate or ammonium carbonate, and tertiary amines such as tri methyl amine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between −20° C. and 200° C., preferably at temperatures between 20° C. and 180° C.

To carry out the process according to the invention for the preparation of compounds of the formula (I), 1 to 15 mol, preferably 1 to 8 mol, of carbonyl halide of the formula (III) or carboxylic anhydride of the formula (IV) are generally employed per mol of the carboxamide of the formula (II).

In general, the process according to the invention is carried out under atmospheric pressure. However, it is also possible to carry out the process at elevated or reduced pressure, in general between 0.1 bar and 10 bar.

The reaction is carried out and the reaction products are worked up and isolated by known methods (cf. also the Preparation Examples).

The substances according to the invention have a powerful microbicidal activity and can be employed in crop protection and the protection of materials for controlling undesirable microorganisms such as fungi and bacteria.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species such as, for example, *Xanthomonas campestris* pv. *oryzae;*

Pseudomonas species such as, for example, *Pseudomonas syringae* pv. *lachrymans;*

Erwinia species such as, for example, *Erwinia amylovora;*

Pythium species such as, for example, *Pythium ultimum;*

Phytophthora species such as, for example, *Phytophthora infestans;*

Pseudoperonospora species such as, for example, *Pseudoperonospora humuli* or *Pseudoperonospora cubensis;*

Plasmopara species such as, for example, *Plasmopara viticola;*

Bremia species such as, for example, *Bremia lactucae;*

Peronospora species such as, for example, *Peronospora pisi* or *P. brassicae;*

Erysiphe species such as, for example, *Erysiphe graminis;*

Sphaerotheca species such as, for example, *Sphaerotheca fuliginea;*

Podosphaera species such as, for example, *Podosphaera leucotricha;*

Venturia species such as, for example, *Venturia inaequalis;*

Pyrenophora species such as, for example, *Pyrenophora teres* or *P. graminea* (conidia form: Drechslera, Syn: Helminthosporium);

Cochliobolus species such as, for example, *Cochliobolus sativus* (conidia form: Drechslera, Syn: Helminthosporium);

Uromyces species such as, for example, *Uromyces appendiculatus;*

Puccinia species such as, for example, *Puccinia recondita;*

Sclerotinia species such as, for example, *Sclerotinia sclerotiorum;*

Tilletia species such as, for example, *Tilletia caries;*

Ustilago species such as, for example, *Ustilago nuda* or *Ustilago avenae;*

Pellicularia species such as, for example, *Pellicularia sasakii;*

Pyricularia species such as, for example, *Pyricularia oryzae;*

Fusarium species such as, for example, *Fusarium culmorum;*

Botrytis species such as, for example, *Botrytis cinerea;*

Septoria species such as, for example, *Septoria nodorum;*

Leptosphaeria species such as, for example, *Leptosphaeria nodorum;*

Cercospora species such as, for example, *Cercospora canescens;*

Alternaria species such as, for example, *Alternaria brassicae;*

Pseudocercosporella species such as, for example, *Pseudocercosporella herpotrichoides.*

The good plant tolerance of the active compounds, at the concentrations required for controlling plant diseases, permits the treatment of aerial parts of plants, of propagation stock and seeds, and of the soil.

The active compounds according to the invention can be employed particularly successfully for controlling cereal diseases such as, for example, against Erysiphe species, Leptosphaeria, Puccinia or Fusarium species, diseases in viticulture, fruit and vegetable production such as, for example, against Venturia and Plasmopara species, or rice diseases such as, for example, against Pyricularia species.

The active compounds according to the invention are also suitable for improving the yield. Moreover, they are of low toxicity and are well tolerated by plants.

In the protection of materials, the substances according to the invention can be employed for protecting industrial materials against infestation with, and destruction by, undesired microorganisms.

Industrial materials in the present context are understood as meaning non-live materials which have been prepared for use in industry. For example, industrial materials which are intended to be protected by the active compounds according to the invention from microbial change or destruction can be glues, sizes, paper and board, textiles, leather, wood, paints and plastic articles, cooling lubricants and other materials which can be infested with, or destroyed by, microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heat-transfer liquids, especially preferably wood.

Examples of microorganisms which are capable of bringing about degradation of, or change in, the industrial materials, which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned by way of example:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia, such as *Escherichia coli,*

Pseudomonas, such as *Pseudomonas aeruginosa* and

Staphylococcus, such as *Staphylococcus aureus.*

Depending on their particular physical and/or chemical properties, the active compounds can be converted into the customary formulations, such as solutions, emulsions, suspensions, powders, foams, pastes, granules, aerosols, microencapsulations in polymeric substances and in coating compositions for seed, and ULV cold and hot fogging formulations.

These formulations are produced in a known manner, for example by mixing the active compounds with extenders, that is, liquid solvents, liquefied gases under pressure, and/or solid carriers, optionally with the use of surfactants, that is, emulsifiers and/or dispersants and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example, mineral oil fractions, alcohols such as butanol or glycol and their ethers and esters, ketones, such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as halogenohydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly-disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, aryl sulphonates, or else protein hydrolysates. Suitable dispersants are: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention, as such or in their formulations, can also be used as a mixture with known fungicides, bactericides, acaricides, nematicides or insecticides, for example to widen the spectrum of action or to prevent the development of resistance. In many cases, synergistic effects are obtained, that is, the activity of the mixture is greater than the activity of the individual components.

Examples of suitable components in mixtures are the following:

Fungicides:
- aldimorph, ampropylfos, ampropylfos-potassium, andoprim, anilazine, azaconazole, azoxystrobin,
- benalaxyl, benodanil, benomyl, benzamacril, benzamacryl-isobutyl, bialaphos, binapacryl, biphenyl, bitertanol, blasticidin-S, bromuconazole, bupirimate, buthiobate,
- calcium polysulfide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
- debacarb, dichlorophen, diclobutrazol, diclofluanid, diclomezin, dicloran, diethofencarb, difenoconazole, dimethirimol, dimethomorph, diniconazole, diniconazol- M, dinocap, diphenylamine, dipyrithion, ditalimfos, dithianon, dodemorph, dodine, drazoxolon,
- ediphenphos, epoxyconazole, etaconazole, ethirimol, etridiazole,
- famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-alminium, fosetyl-sodium, fthalide, fuberidazole, furalaxyl, furametpyr, furcarbonil, furconazole, furconazole-cis, furmecyclox,
- guazatine,
- hexachlorobenzene, hexaconazole, hymexazol,
- imazalil, imibenconazole, iminoctadine, iminoctadine albesilate, iminoctadine triacetate, iodocarb, ipconazol, iprobenfos (IBP), iprodione, irumamycin, isoprothiolane, isovaledione,
- kasugamycin, kresoxim-methyl, copper preparations such as: copper hydroxide, copper naphthenate, copper oxychloride, copper sulfate, copper oxide, oxine-copper and Bordeaux mixture,
- mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
- nickel dimethyldithiocarbamate, nitrothal-isopropyl, nuarimol,
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
- quinconazole, quintozene (PCNB),
- sulphur and sulphur preparations,
- tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
- uniconazole,
- validamycin A, vinclozolin, viniconazole,
- zarilamid, zineb, ziram or else
- Dagger G,
- OK-8705,
- OK-8801,
- α-(1,1 -dimethylethyl)-β-(2-phenoxyethyl)-1H-1,2,4-triazol-1-ethanol,
- α-(2,4-dichlorophenyl)-β-fluoro-b-propyl-1H-1,2,4-triazol-1-ethanol,
- α-(2,4-dichlorophenyl)-β-methoxy-a-methyl-1H-1,2,4-triazol-1-ethanol,
- α-(5-methyl-1,3-dioxan-5-yl)-β-[[4-(trifluoromethyl)-phenyl]-methylene]-1H-1,2,4-triazole-1-ethanol,
- (5RS,6RS)-6-hydroxy-2,2,7,7-tetramethyl-5-(1H-1,2,4-triazol-1-yl)-3-octanone,
- (E)-a-(methoxyimino)-N-methyl-2-phenoxy-phenylacetamide,
- 1-isopropyl{2-methyl-1-[[[1-(4-methylphenyl)-ethyl]-amino]-carbonyl]-propyl}-carbamate
- 1-(2,4-dichlorophenyl)-2-(1H-1,2,4-triazol-1-yl)-ethanone O-(phenylmethyl)oxime,
- 1-(2-methyl-1-naphthalenyl)-1H-pyrrole-2,5-dione,
- 1-(3,5-dichlorophenyl)-3-(2-propenyl)-2,5-pyrrolidinedione,
- 1-[(diiodmethyl)-sulfonyl]4-methyl-benzene,
- 1-[[2-(2,4-dichlorophenyl)-1,3-dioxolan-2-yl]-methyl]-1H-imidazole,
- 1-[[2-(4-chlorophenyl)-3-phenyloxiranyl]-methyl]-1H-1,2,4-triazole,
- 1-[1-[2-[(2,4-dichlorophenyl)-methoxy]-phenyl]-ethenyl]-1H-imidazole,
- 1-methyl-5-nonyl-2-(phenylmethyl)-3-pyrrolidinole,
- 2,'6'-dibromo-2-methyl-4'-trifluoromethoxy-4'-trifluoromethyl-1,3-thiazole-5-carboxanilide,
- 2,2-dichloro-N-[1-(4chlorophenyl)-ethyl]-1-ethyl-3-methyl-cyclopropanecarboxamide,
- 2,6-dichloro-5-(methylthio)4-pyrimidinyl-thiocyanate,
- 2,6-dichloro-N-(4-trifluoromethylbenzyl)-benzamide,
- 2,6-dichloro-N-[[4-(trifluoromethyl)-phenyl]-methyl]-benzamide,
- 2-(2,3,3-triiodo-2-propenyl)-2H-tetrazole,
- 2-[(1-methylethyl)-sulfonyl]-5-(trichloromethyl)-1,3,4-thiadiazole,
- 2-[[6-deoxy-4-O-(4-O-methyl-β-D-glycopyranosyl)-a-D-glucopyranosyl]-amino]-4-methoxy-1H-pyrrolo[2,3-d]pyrimidin-5-carbonitrile, 2-aminobutane, 2-bromo-2-(bromomethyl)-pentandinitrile, 2-chloro-N-(2,3-dihydro-1,1,3-trimethyl-1H-inden-4-yl)-3-pyridincarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl )-N-ethyl-N-propyl-1,4-dioxaspiro[4.5] decane-2-methanamine, 8-hydroxyquinoline sulfate, 9H-xanthene-9-carboxylic acid 2-[(phenylamino)-carbonyl]-hydrazide, bis-(1-methylethyl)-3-methyl4-3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium hydrogen carbonate, sodium methanetetrathiolate, methyl 1-(2,3-dihydro-2,2-dimethyl-1H-inden-1-yl)-1H-imidazol-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexancarboxamide.

N-(2,6-dimethylphenyl)-2-methoxy-N-(tetrahydro-2-oxo-3-furanyl)-acetamide,

N-(2,6-dimethylphenyl)-2-methoxy-N-(tetrahydro-2-oxo-3-thienyl)-acetamide,

N-(2-chloro-4-nitrophenyl)-4-methyl-3-nitro-benzenesulfonamide,

N-(4-cyclohexylphenyl)-1,4,5,6-tetrahydro-2-pyrimidinamine,

N-(4-hexylphenyl)-1,4,5,6-tetrahydro-2-pyrimidinamine,

N-(5-chloro-2-methylphenyl)-2-methoxy-N-(2-oxo-3-oxazolidinyl)-acetamide,

N-(6-methoxy)-3-pyridinyl)-cyclopropancarboxamide,

N-[2,2,2-trichloro-1-[(chloroacetyl)-amino]-ethyl]-benzamide,

N-[3-chloro-4,5-bis-(2-propinyloxy)-phenyl]-N'-methoxy-methaneimidamide, sodium N-formyl-N-hydroxy-DL-alanine, O,O-diethyl[2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran]-3'-one.

Bactericides:

bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:

abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(trifluoro-methyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanirnidamide, chlorpyrifos, chlorpyrifos M, cis-resmethrin, clocythrin, clofentezin, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lamda-cyhalothrin, lufenuron, malathion, mecarbam, mevinphos, mesulfenphos, metaldehyde, methacrifos, methamidophos, methidathion, methiocarb, methomyl, metolcarb, milbemectin, mono-crotophos, moxidectin, naled, NC 184, nitenpyram ometboate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiophos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds such as herbicides, or with fertilizers and growth regulators, is also possible.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, broadcasting, dusting, foaming, brushing on and the like. It is furthermore possible to apply the active compounds by the ultra-low volume method, or to inject the active compound formulation or the active compound itself into the soil. The seed of the plants can also be treated.

When applying the active compounds as fungicides, the rates of application can be varied within a substantial range, depending on the type of application. For the treatment of parts of plants, the rates of application of active compound are, in general, between 0.1 and 10,000 g/ha, preferably between 10 and 1,000 g/ha. For the treatment of seed, the rates of application of active compound are generally between 0.001 and 50 g per kilogram of seed, preferably between 0.01 and 10 g, per kilogram of seed. For the treatment of soil, the rates of application of active compound are generally between 0.1 and 10,000 g/ha, preferably between 1 and 5,000 g/ha.

The compositions used for the protection of industrial materials comprise the active compounds in general in an amount of 1 to 95%, preferably 10 to 75%.

The use concentrations of the active compounds according to the invention depend on the species and the occurrence of the microorganisms to be controlled and on the composition of the material to be protected. The optimum rate can be determined by test series. In general, the use concentrations are in the range of 0.001 to 5% by weight, preferably 0.05 to 1.0% by weight, based on the material to be protected.

The efficacy and the spectrum of action of the active compounds to be used according to the invention in the protection of materials, or of the compositions, concentrates or, quite generally, formulations which can be prepared from them, can be increased by adding, if appropriate, further antimicrobially active compounds, fungicides, bactericides, herbicides, insecticides or other active compounds to widen the spectrum of action or to achieve specific effects, such as, for example, additional protection against insects. These mixtures may have a wider spectrum of action than the compounds according to the invention.

PREPARATION EXAMPLES

Example (1)

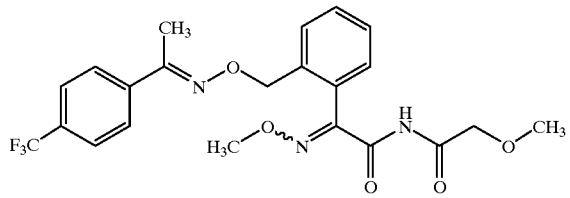

A solution of 2.3 g (0.006 mol) of 2-methoxyimino-2-{2-[1-(4-trifluoromethylphenyl)-ethylideneaminooxymethyl]-phenyl}-acetamide and 0.6 g (0.0075 mol) of pyridine in 20 ml of toluene is heated at approx. 90° C. A solution of 6.5 g (0.06 mol) of methoxyacetyl chloride in 20 ml of toluene is added dropwise at this temperature and the mixture is stirred for 24 hours at 90° C. After cooling, the reaction mixture is extracted by shaking with water. The organic phase is separated off, dried over sodium sulphate and concentrated in vacuo. The residue is chromatographed on silica gel using cyclohexane/ethyl acetate (9:1 to 3:1). This gives 0.6 g (22% of theory) of 2-methoxy-N-(methoxyimino-{2-[1-(4-trifluoromethylphenyl)-ethylideneaminooxymethyl]-phenyl}-acetyl)-acetamide of melting point 134–138° C.

Example (2)

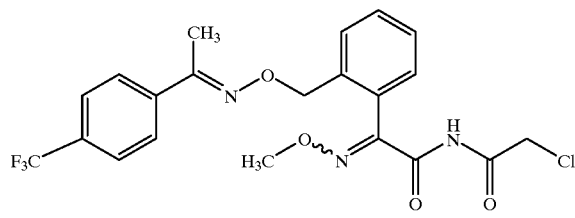

A solution of 2.3 g (0.006 mol) of 2-methoxyimino-2-{2-[1-(4-trifluoromethyl-phenyl)-ethylideneaminooxymethyl]-phenyl}-acetamide and 0.6 g (0.0075 mol) of pyridine in 20 ml of toluene is heated at approx. 90° C. A solution of 6.8 g (0.06 mol) of chloroacetyl chloride in 20 ml of toluene is added dropwise at this temperature and the mixture is stirred for 24 hours at 90° C. After cooling, the reaction mixture is extracted by shaking with water. The organic phase is separated off, dried over sodium sulphate and concentrated in vacuo. The residue is chromatographed of 3 silica gel using cyclohexane/ethyl acetate (19:1). This gives 0.3 g (11% of theory) of 2-chloro-N-(methoxyimino-{2-[1-(4-trifluoromethylphenyl)-ethylideneaminooxymethyl]-phenyl}-acetyl)-acetamide of melting point 92° C. (decomp.).

Other compounds of the formula (I) according to the invention which can be obtained analogously to Examples (1) and (2) and in accordance with the general description of the preparation process according to the invention are those listed in Table 1 below:

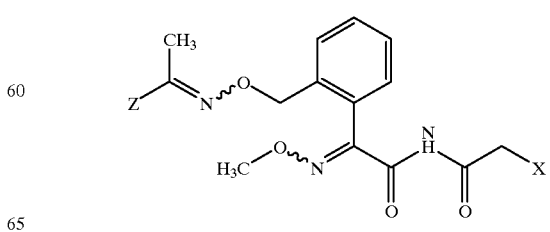

TABLE 1

| Ex. No. | X | Z | LogP*) | M.p. (° C.) |
|---|---|---|---|---|
| 3 | —O—CH₃ | 4-ethylphenyl | 3.99 | |
| 4 | —O—CH₃ | 4-fluorophenyl | 3.37 | |
| 5 | —O—CH₃ | 3-trifluoromethylphenyl | 3.88 | 98–101 |
| 6 | —O—CH₃ | 5-indanyl (2,3-dihydro-1H-inden-5-yl) | 4.09 | |
| 7 | —O—CH₃ | 4-bromophenyl | 3.87 | 109–112 |
| 8 | —O—CH₃ | 4-(2,2,2-trifluoroethoxy)phenyl | 3.74 | |
| 9 | —Cl | 4-ethylphenyl | 4.36 | |
| 10 | —O—CH₃ | 3-chlorophenyl | 3.74 | |
| 11 | —Cl | 5-indanyl (2,3-dihydro-1H-inden-5-yl) | 4.47 | |
| 12 | —Cl | 4-fluorophenyl | 3.73 | |
| 13 | —Cl | 4-(2,2,2-trifluoroethoxy)phenyl | 4.05 | |
| 14 | —Cl | 3-chlorophenyl | 4.10 | |
| 15 | —O—CH₃ | 4-(1,1,1-trifluoropropan-2-yloxy)phenyl | 4.02 | |
| 16 | —Cl | 4-(1,1,1-trifluoropropan-2-yloxy)phenyl | 4.32 | |
| 17 | —O—CH₃ | 4-(2,2,3,3,3-pentafluoropropoxy)phenyl | 4.20 | |
| 18 | —O—CH₃ | 3,4-dichlorophenyl | 4.19 | |
| 19 | —Cl | 3,4-dichlorophenyl | 4.52 | |
| 20 | —O—CH₃ | 4-chlorophenyl | 3.76 | |
| 21 | —Cl | 4-chlorophenyl | 4.12 | |
| 22 | —O—CH₃ | 4-tolyl | 3.62 | |
| 23 | —Cl | 4-tolyl | 4.00 | |
| 24 | —O—CH₃ | 3,4-dimethylphenyl | 3.88 | |
| 25 | —Cl | 3,4-dimethylphenyl | 4.26 | |
| 26 | —O—CH₃ | phenyl | 3.27 | |
| 27 | —Cl | phenyl | 3.66 | |
| 28 | —O—CH₃ | 4-difluoromethoxyphenyl | 3.49 | |
| 29 | —Cl | 4-difluoromethoxyphenyl | 3.81 | |
| 30 | —O—CH₃ | 3-trifluoromethoxyphenyl | | |
| 31 | —O—C₂H₅ | 3-trifluoromethoxyphenyl | | |
| 32 | Cl | 3-trifluoromethoxyphenyl | | |

TABLE 1-continued

| Ex. No. | X | Z | LogP*) | M.p. (° C.) |
|---|---|---|---|---|
| 33 | —O—CH₃ | (structure: 4-methylphenyl-O-C(=CH₂)-CH₂F) | | |
| 34 | Cl | (structure: 4-methylphenyl-O-C(=CH₂)-CH₂F) | | |
| 35 | —O—CH₃ | 2-fluoro-4-methoxyphenyl | 3.32 | |
| 36 | —O—C₂H₅ | 2-fluoro-4-methoxyphenyl | | |
| 37 | Cl | 2-fluoro-4-methoxyphenyl | | |
| 38 | —O—CH₃ | 4-fluoro-2-methoxyphenyl | 3.32 | |
| 39 | Cl | 4-fluoro-2-methoxyphenyl | | |
| 40 | —O—CH₃ | 4-ethoxy-2-fluorophenyl | 3.67 | |
| 41 | —O—CH₃ | 2,4-dichloro-5-fluoro-phenyl | 4.09 | |
| 42 | Cl | 2,4-dichloro-5-fluoro-phenyl | 4.44 | |
| 43 | Cl | 3,4-dimethoxyphenyl | 3.21 | |
| 44 | —O—CH₃ | 3,4-dimethoxyphenyl | 2.85 | |
| 45 | —O—C₂H₅ | 3,4-dimethoxyphenyl | | |

*The logP values were determined as specified in EEC Directive 79/831 Annex V. A8 by HPLC (gradient method, acetonitrile/0.1% aqueous phosphoric acid)

Use Examples

Example A

*Fusarium Nivale* (var. *nivale*) Test (wheat)/Protective

| | | |
|---|---|---|
| Solvent: | 25 | parts by weight of N,N-dimethylacetamide |
| Emulsifier: | 0.6 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried, the plants are sprayed with a conidial suspension of *Fusarium nivale* (var. *nivale*).

The plants are placed in a greenhouse under translucent incubation cloches at a temperature of approximately 15° C. and a relative atmospheric humidity of approximately 100%.

The test is evaluated 4 days after the inoculation. 0% means an efficacy which corresponds to that of the control, while an efficacy of 100% means no disease is observed.

In this test, an efficacy of 95% or more is shown by the substances according to the invention listed in Examples (10), (19) and (20) at a rate of application of 250 g/ha.

Example B

Erysiphe Test (barley)/Curative

| | | |
|---|---|---|
| Solvent: | 25 | parts by weight of N,N-dimethylactamide |
| Emulsifier: | 0.6 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f.sp. hordei. 48 hours after the inoculation, the plants are sprayed with the preparation of active compound at the stated rate of application.

The plants are placed in a greenhouse at a temperature of approximately 20° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

In this test, an efficacy of 95% or more is shown by the substance according to the invention listed in Example (14) at a rate of application of 250 g/ha.

Example C

*Leptosphaeria Nodorum* Test (wheat)/Protective

| | | |
|---|---|---|
| Solvent: | 25 | parts by weight of N,N-dimethylacetamide |
| Emulsifier: | 0.6 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are sprayed with a spore suspension of *Leptosphaeria nodorum*. The plants remain in an incubation cabinet for 48 hours at 20° C. and a relative atmospheric humidity of 100%.

The plants are placed in a greenhouse at a temperature of approximately 15° C. and a relative atmospheric humidity of 80%.

The test is evaluated 10 days after the inoculation. 0% means an efficacy which corresponds to that of the control, while an efficacy of 100% means no disease is observed.

In this test, an efficacy of 95% or more is shown by the substances according to the invention listed in Examples (19), (20) and (21) at a rate of application of 250 g/ha.

Example D

Puccinia Test (wheat)/Protective

| Solvent: | 25 | parts by weight of N,N-Dimethylacetamide |
|---|---|---|
| Emulsifier: | 0.6 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are sprayed with a conidial suspension of *Puccinia recondita*. The plants remain in an incubation cabinet for 48 hours at 20° C. and a relative atmospheric humidity of 100%.

The plants are then placed in a greenhouse at a temperature of approximately 20° C. and a relative atmospheric humidity of 80%, to promote the development of rust pustules.

The test is evaluated 10 days after the inoculation. 0% means an efficacy which corresponds to that of the control, while an efficacy of 100% means no disease is observed.

In this test, an efficacy of 95% or more is shown by the substances according to the invention listed in Examples (5), (19) and (22) at a rate of application of 250 g/ha.

Example E

Erysiphe Test (barley)/Protective

| Solvent: | 25 | parts by weight of N,N-dimethylacetamide |
|---|---|---|
| Emulsifier: | 0.6 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application.

After the spray coating has dried on, the plants are dusted with the spores of *Erysiphe graminis* f.sp. hordei.

The plants are placed in a greenhouse at a temperature of approximately 20° C. and a relative atmospheric humidity of approximately 80%, to promote the development of mildew pustules.

The test is evaluated 7 days after the inoculation. 0% means an efficacy which corresponds to that of the control, while an efficacy of 100% means no disease is observed.

In this test, an efficacy of 100% or more is shown by the substances according to the invention listed in Examples (5), (13), (14), (15) and (18) at a rate of application of 250 g/ha.

Example F

Erysiphe Test (wheat)/Protective

| Solvent: | 25 | parts by weight of N,N-dimethylacetamide |
|---|---|---|
| Emulsifier: | 0.6 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application.

After the spray coating has dried on, the plants are dusted with the spores of *Erysiphe graminis* f.sp. tritici.

The plants are placed in a greenhouse at a temperature of approximately 20° C. and a relative atmospheric humidity of approximately 80%, to promote the development of mildew pustules.

The test is evaluated 7 days after the inoculation. 0% means an efficacy which corresponds to that of the control, while an efficacy of 100% means no disease is observed.

In this test, an efficacy of 95% or more is shown by the substance according to the invention listed in Example (5) at a rate of application of 250 g/ha.

Example G

*Fusarium Graminearum* Test (barley)/Protective

| Solvent: | 25 | parts by weight of N,N-dimethylacetamide |
|---|---|---|
| Emulsifier: | 0.6 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are sprayed with a conidial suspension of *Fusarium graminearum*.

The plants are placed in a greenhouse under transluscent incubation cloches at a temperature of approximately 15° C. and a relative atmospheric humidity of 100%.

The test is evaluated 4 days after the inoculation. 0% means an efficacy which corresponds to that of the control, while an efficacy of 100% means no disease is observed.

Example H

Plasmopara Test (grapevines)/Protective

| Solvent: | 47 | parts by weight of acetone |
|---|---|---|
| Emulsifier: | 3 | parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100% The plants are subsequently placed for 5 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the control, while an efficacy of 100% means no disease is observed.

In this test, an efficacy of 90% or more is shown by the substances according to the invention listed in Examples (1), (3), (5), (9), (10), (11), (12), (13), (14), (15), (16), (18), (19), (20), (21), (25) and (27) at a rate of application of 100 g/ha.

Example I

Venturia Test (apple)/Protective

| Solvent: | 47 | parts by weight of acetone |
|---|---|---|
| Emulsifier: | | parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous conidial suspension of the apple scab pathogen *Venturia inaequalisa* and then remain in an incubation cabinet for 1 day at approx. 20° C. and a relative atmospheric humidity of 100%.

The plants are then placed in a greenhouse at approx. 21° C. and a relative atmospheric humidity of approx. 90%.

The test is evaluated 12 days after the inoculation. 0% means an efficacy which corresponds to that of the control, while an efficacy of 100% means no disease is observed.

In this test, an efficacy of 95% or more is shown by the substance according to the invention listed in Examples (3), (6), (8), (9) and (11) at a rate of application of 10 g/ha.

Example K

Pyricularia Test (rice)/Protective

| Solvent: | 25 | parts by weight of N,N-dimethylacetamide |
|---|---|---|
| Emulsifier: | 0.06 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young rice plants are sprayed with the preparation of active compound at the stated rate of application. After the spray coating has dried on, the plants are inoculated with an aqueous spore suspension of *Pyricularia oryzae*. The plants are subsequently placed in a greenhouse at 25° C. and a relative atmospheric humidity of 100%.

The test is evaluated 4 days after the inoculation. 0% means an efficacy which corresponds to that of the control, while an efficacy of 100% means no disease is observed.

In this test, an efficacy of 70% or more is shown by the substance according to the invention listed in Examples (5), (7), (8), (9), (10), (11), (16), (18), (19), (20) and (22) at a rate of application of 125 g/ha.

What is claimed is:

1. Compounds of the formula (I)

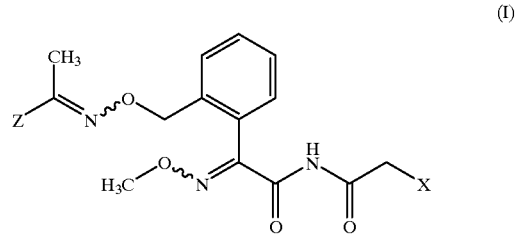

in which
X represents halogen or alkoxy and
Z represents unsubstituted or substituted aryl or a group

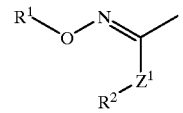

in which
$R^1$ represents unsubstituted or substituted alkyl, cycloalkyl or arylalkyl,
$R^2$ represents unsubstituted or substituted alkyl, aryl, cycloalkyl, arylalkyl, heterocyclyl or heterocyclylalkyl,
$Z^1$ represents a single bond, oxygen, sulphur or a group

where
$R^4$ represents alkyl, or together with $R^2$ and the nitrogen atom to which they are bonded forms an unsubstituted or substituted heterocyclic ring.

2. Compounds of the formula (I) according to claim 1 in which

X represents chlorine or alkoxy having 1 to 4 carbon atoms.

3. Compounds of the formula (I) according to claim 1 in which

Z represents phenyl or naphthyl, each of which is unsubstituted, monosubstituted or polysubstituted by identical or different substituents, the substituents being selected from the list hereinbelow:

halogen, cyano, nitro, hydroxyl, formyl, carboxyl, carbamoyl, thiocarbamoyl;

in each case straight-chain or branched alkyl, alkoxy, alkylthio, alkylsulphinyl or alkylsulphonyl, each of which have 1 to 6 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy each of which has 2 to 6 carbon atoms and 1 to 11 identical or different halogen atoms;

in each case straight-chain or branched alkylcarbonyl, alkylcarbonyloxy, alkoxycarbonyl or alkylsulphonyloxy, each of which has 1 to 6 carbon atoms in the individual alkyl moieties;

in each case divalent alkylene or dioxyalkylene, each of which has 1 to 6 carbon atoms and each of which is unsubstituted, monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl, each of which has 3 to 7 ring members of which in each case 1 to 3 are identical or different heteroatoms—in particular nitrogen, oxygen and/or sulphur- or a group

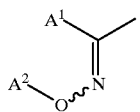

in which
$A^1$ represents alkyl with 1 to 4 carbon atoms or cycloalkyl having 1 to 6 carbon atoms and
$A^2$ represents alkyl having 1 to 4 carbon atoms, alkenyl or alkinyl, each of which has 2 to 4 carbon atoms, unsubstituted or substituted by cyano, alkoxy, alkylthio, alkylamino, dialkylamino or phenyl, Z also represents a group

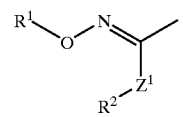

in which
$R^1$ represents alkyl having 1 to 12 carbon atoms, cycloalkyl having 3 to 8 carbon atoms which is unsubstituted or substituted by halogen or alkyl having 1 to 4 carbon atoms, or arylalkyl having 6 to 10 carbon atoms in the aryl moiety and 1 to 4 carbon atoms in the alkyl moiety, and which is unsubstituted or substituted in the aryl moiety, the substituents being selected from the following list:

halogen, cyano, nitro, in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl, each of which has 1 to 8 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

$R^2$ represents alkyl having 1 to 12 carbon atoms, cycloalkyl having 3 to 8 carbon atoms which is unsubstituted or substituted by halogen or alkyl having 1 to 4 carbon atoms, or represents heterocyclyl, benzoheterocyclyl, dibenzoheterocyclyl or heterocyclylalkyl, each of which has 3 to 7 ring members in the heterocyclyl moiety and 1 to 4 carbon atoms in the alkyl moiety and each of which is unsubstituted or substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl;

or represents aryl or arylalkyl having 6 to 10 carbon atoms in the aryl moiety and 1 to 4 carbon atoms in the alkyl moiety, each of which is unsubstituted or substituted in the aryl moiety, the substituents being selected from the following list:

halogen, cyano, nitro, amino, carbamoyl, thiocarbamoyl; in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl, each of which has 1 to 8 carbon atoms;

in each case straight-chain or branched alkenyl or alkenyloxy, each of which has 2 to 6 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy each of which has 2 to 6 carbon atoms and 1 to 11 identical or different halogen atoms;

in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;

cycloalkyl or cycloalkyloxy, each of which has 3 to 6 carbon atoms;

in each case divalent alkylene having 3 or 4 carbon atoms, oxyalkylene having 2 or 3 carbon atoms or dioxyalkylene having 1 or 2 carbon atoms, in each case unsubstituted or monosubstituted to tetrasubstituted by identical or different substituents from the series consisting of fluorine, chlorine, methyl, trifluoromethyl or ethyl;

phenoxy or phenylalkoxy having 1 to 4 carbon atoms in the alkyl moiety and in each case unsubstituted or substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclyloxy, heterocyclylthio, heterocyclylsulphinyl or heterocyclylsulphonyl having 5 or 6 ring members, in each case unsubstituted or substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl, or a group

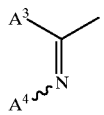

in which $A^3$ represents hydrogen or alkyl having 1 to 4 carbon atoms or cycloalkyl having 3 to 6 carbon atoms and $A^4$ represents hydroxyl, amino, methylamino, methyl, phenyl, benzyl, alkoxy, alkylamino, dialkylamino having 1 to 4 carbon atoms in the respective alkyl chains, $Z^1$ represents a single bond, oxygen, sulphur or a group

in which $R^4$ represents alkyl having 1 to 4 carbon atoms, or together with $R^2$ and the nitrogen atom to which they are bonded forms an unsubstituted or substituted, 3 to 6-membered, heterocyclic ring.

4. Compound of the formula (I) in which

X represents chlorine, methoxy, ethoxy, n- or i-propoxy, n-, i-, s- or t-butoxy.

5. Compounds of the formula (I) according to claim 1 in which

Z represents phenyl which is unsubstituted or substituted, the substituents being selected from the following list:
fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, 3-fluoropropen-2-yloxy, methoxycarbonyl, ethoxycarbonyl, in each case divalent propane-1,3-diyl, butane-1,4-diyl, methylenedioxy or ethylenedioxy, each of which is unsubstituted or monosubstituted to tetrasubstituted by identical or different substituents from the series consisting of fluorine, chlorine, methyl, trifluoromethyl or ethyl, or a group

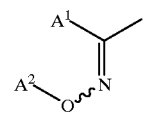

in which $A^1$ represents, in particular, methyl, ethyl, n- or i-propyl, n-, i-, s- or t-butyl, cyclopropyl or cyclobutyl, and $A^2$ represents, in particular, methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, Z likewise represents a group

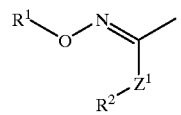

in which $R^1$ represents cyclopentyl or cyclohexyl, each of which is unsubstituted or monosubstituted to tetrasubstituted by fluorine, chlorine, methyl or ethyl; or represents cyclopropyl, cyclobutyl, cyclopentyl or cyclohexyl, unsubstituted or substituted by methyl, ethyl, fluorine, chlorine or bromine;

or represents benzyl, 1-phenylethyl or 2-phenylethyl, each of which is unsubstituted or monosubstituted to tetrasubstituted by identical or different substituents, the substituents being selected from the following list:
fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethyl sulphonyl, methylaminomethyl, dimethylaminomethyl, trifluoromethyl, trifluoroethyl, difluoromethoxy, trifluoromethoxy, difluorochloromethoxy, trifluoroethoxy, pentafluoroethoxy, 2-chloro-1, 1,2-trifluoroethoxy, difluoromethylthio, trifluoromethylthio, difluorochloromethylthio, trifluoromethylsulphinyl or trifluoromethylsulphonyl, $R^2$ represents methyl, ethyl, n- or i-propyl, n-, i-, s- or t-butyl, pentyl, hexyl, heptyl, octyl, nonyl, decyl, undecyl, dodecyl, cyclopentyl or cyclohexyl, each of which is unsubstituted or monosubstituted to tetrasubstituted by fluorine, chlorine, methyl or ethyl; or represents thienyl, pyridyl, furyl, piperazinyl, thiazolyl, dioxazinyl, benzimidazolyl, benzothiazolyl, benzofuranyl, benzopyrazolyl, dibenzothiazinyl, thienylmethyl, pyridylmethyl or furylmethyl, each of which is unsubstituted or substituted by methyl, ethyl, fluorine, chlorine, bromine, trifluoromethyl, phenyl;

or represents phenyl, benzyl, 1-phenylethyl or 2-phenylethyl, each of which is unsubstituted or monosubstituted to tetrasubstituted in the phenyl moiety by identical or different substituents, the substituents being selected from the following list:
fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyl oxy, 2-methylallyloxy, propen-1-yloxy, crotonyloxy, propargyloxy; trifluoromethyl, trifluoroethyl, difluoromethoxy, trifluoromethoxy, difluorochloromethoxy, trifluoroethoxy, pentafluoroethoxy, 2-chloro-1, 1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy, in each case divalent propanediyl, ethylenoxy, methylenedioxy, ethylene dioxy, each of which is unsubstituted or monosubstituted to tetrasubstituted by identical or different substituents from the series consisting of fluorine, chlorine, methyl or trifluoromethyl, phenoxy or benzyl, each of which is unsubstituted or substituted by fluorine, chlorine, methyl, trifluoromethyl or methoxy, heterocyclyl, heterocyclyloxy, heterocyclylthio, hetereocyclylsulphinyl or heterocyclylsulphonyl, each of which has 5 or 6 ring members and is unsubstituted or substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl, or represents thienyl, imidazolyl, thiadiazolyl, pyridyl, furyl, piperazinyl, thiazolyl, dioxazinyl, thiadiazolylsulphonyl, optionally substituted by methyl, ethyl, fluorine, chlorine, bromine, trifluoromethyl, phenyl;

or a group

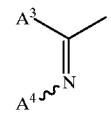

in which
$A^3$ represents hydrogen or methyl and
$A^4$ represents hydroxyl, methoxy, ethoxy, amino, methylamino, methyl, phenyl or benzyl,
$Z^1$ represents a single bond, oxygen, sulphur or a group

in which
$R^4$ represents methyl, ethyl, n- or i-propyl, n-, i-, s- or t-butyl, or together with $R^2$ and the nitrogen atom to which they are bonded forms an unsubstituted or substituted 5 to 6-membered heterocyclic ring.

6. Compositions comprising a compound of the formula (I) according to claim 1 and an ingredient selected from the group consisting of extenders, carriers, surfactants and mixtures thereof.

7. Method of controlling microorganisms, comprising the step of applying compounds of the formula (I) according to claim 1 to mircoorganisms and/or their environment.

8. Method of controlling microorganisms, comprising the step of applying compositions according to claim 6 to microorganisms and/or their environment.

9. Process for the preparation of compositions, characterized in that compounds of the formula (I) according to claim 1 are mixed with an ingredient selected from the group consisting of extenders, carriers, surfactants and mixtures thereof.

10. Process for the preparation of compounds of the formula (I) as defined in claim 1, characterized in that carboxamides of the formula (II)

(II)

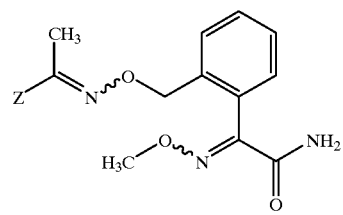

in which

Z is as defined above, are reacted with an carbonyl halide of the formula (III),

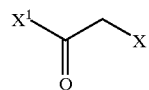
(III)

in which
X is as defined above, and
X¹ represents halogen, or
are reacted with a carboxylic anhydride of the formula (IV)

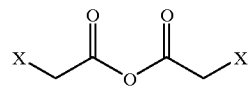
(IV)

in which

X has the meaning given above.

11. A compound according to claim 5, wherein Z represents phenyl which is monosubstituted or disubstituted.

12. A compound according to claim 5, wherein Z represents phenyl which is substituted in the 3- and/or 4-position.

13. A process according to claim 10 wherein the process occurs in the presence of a diluent.

14. A process according to claim 10 wherein the process occurs in the presence of an acid binder.

15. A method according to claim 7, wherein the microorganism is selected from the group consisting of bacteria, fungi, yeasts, algae, slime organisms and mixtures thereof.

16. A method according to claim 7, wherein the microorganism is selected from the group consisting of bacteria, fungi, yeasts, algae, slime organisms and mixtures thereof.

* * * * *